(12) United States Patent
Alelov

(10) Patent No.: US 10,980,283 B2
(45) Date of Patent: *Apr. 20, 2021

(54) INHALATION DEVICE INCLUDING SUBSTANCE USAGE CONTROLS

(71) Applicant: Logic Technology Development, LLC, Pompano Beach, FL (US)

(72) Inventor: Eli Alelov, Pompano Beach, FL (US)

(73) Assignee: Logic Technology Development, LLC, Pompano Beach, FL (US)

( * ) Notice: Subject to any disclaimer, the term of this patent is extended or adjusted under 35 U.S.C. 154(b) by 139 days.

This patent is subject to a terminal disclaimer.

(21) Appl. No.: 16/288,841

(22) Filed: Feb. 28, 2019

(65) Prior Publication Data

US 2019/0191774 A1    Jun. 27, 2019

Related U.S. Application Data

(63) Continuation of application No. 14/257,079, filed on Apr. 21, 2014, now Pat. No. 10,420,373, which is a
(Continued)

(51) Int. Cl.
*A61M 11/00* (2006.01)
*A24F 47/00* (2020.01)
(Continued)

(52) U.S. Cl.
CPC ............ *A24F 47/008* (2013.01); *A24F 40/50* (2020.01); *A61M 11/005* (2013.01);
(Continued)

(58) Field of Classification Search
CPC .. A24F 47/008; A61M 11/005; A61M 11/042; A61M 15/0003; A61M 15/008;
(Continued)

(56) References Cited

U.S. PATENT DOCUMENTS 4,050,629 A    9/1977 Query et al.
4,106,503 A    8/1978 Rosenthal et al.
(Continued)

FOREIGN PATENT DOCUMENTS

AU    677081 B2    4/1997
CA    2641869 A1   5/2010
(Continued)

OTHER PUBLICATIONS

Communication on EP Application 11820510.3, dated Aug. 27, 2014.
(Continued)

*Primary Examiner* — Steven O Douglas
(74) *Attorney, Agent, or Firm* — Lerner, David, Littenberg, Krumholz & Mentlik, LLP

(57) ABSTRACT

A smoke inhalation apparatus may include a cartridge having a release device configured to release a substance, a controller configured to control the operation of the release device, and a communication device configured to allow a user to change and monitor settings of the smoke inhalation apparatus and/or a state of the smoke inhalation apparatus. The communication device may include a display configured to indicate usage of the smoke inhalation apparatus. The communication device may be configured to reprogram the controller to operate according to a modified usage limit different than an initial usage limit.

20 Claims, 8 Drawing Sheets

Related U.S. Application Data continuation of application No. 13/460,982, filed on May 1, 2012, now Pat. No. 8,714,150, which is a continuation of application No. 13/215,728, filed on Aug. 23, 2011, now Pat. No. 8,550,069.

(60) Provisional application No. 61/402,136, filed on Aug. 24, 2010.

(51) Int. Cl.
| | |
|---|---|
| *A61M 15/00* | (2006.01) |
| *A61M 15/06* | (2006.01) |
| *A61M 11/04* | (2006.01) |
| *A24F 40/50* | (2020.01) |
| *A61M 16/00* | (2006.01) |

(52) U.S. Cl.
CPC ...... *A61M 11/042* (2014.02); *A61M 15/0003* (2014.02); *A61M 15/008* (2014.02); *A61M 15/0065* (2013.01); *A61M 15/0066* (2014.02); *A61M 15/0083* (2014.02); *A61M 15/06* (2013.01); *A61M 15/0085* (2013.01); *A61M 2016/0021* (2013.01); *A61M 2016/0024* (2013.01); *A61M 2205/3306* (2013.01); *A61M 2205/3368* (2013.01); *A61M 2205/3375* (2013.01); *A61M 2205/502* (2013.01); *A61M 2205/583* (2013.01); *A61M 2205/8206* (2013.01)

(58) Field of Classification Search
CPC .............. A61M 15/0065; A61M 15/15; A61M 15/0066; A61M 15/0083; A61M 15/06; A61M 15/0085; A61M 2016/0021; A61M 2016/0024; A61M 2205/3306; A61M 2205/3368; A61M 2205/3375; A61M 2205/502; A61M 2205/583; A61M 2205/8206
See application file for complete search history.

(56) References Cited

U.S. PATENT DOCUMENTS

| | | | |
|---|---|---|---|
| 4,141,369 A | 2/1979 | Burruss | |
| 4,945,928 A | 8/1990 | Rose | |
| 5,060,671 A | 10/1991 | Counts et al. | |
| 5,372,148 A | 12/1994 | McCafferty et al. | |
| 5,479,948 A | 1/1996 | Counts et al. | |
| 5,649,554 A | 7/1997 | Sprinkel et al. | |
| 5,666,977 A | 9/1997 | Higgins et al. | |
| 5,934,289 A | 8/1999 | Watkins et al. | |
| 5,970,973 A | 10/1999 | Gonda et al. | |
| 6,196,218 B1 | 3/2001 | Voges | |
| 6,234,167 B1 | 5/2001 | Cox et al. | |
| 6,260,549 B1 | 7/2001 | Sosiak | |
| 6,516,796 B1 | 2/2003 | Cox et al. | |
| 6,772,756 B2 | 8/2004 | Shayan | |
| 7,481,226 B2 | 1/2009 | Cholet | |
| 7,726,320 B2 | 6/2010 | Robinson et al. | |
| 7,905,230 B2 | 3/2011 | Schuler et al. | |
| 8,156,944 B2 | 4/2012 | Han | |
| 9,352,288 B2 | 5/2016 | Terry et al. | |
| 10,524,516 B2 * | 1/2020 | Alelov | A61M 15/0083 |
| 2002/0079309 A1 | 6/2002 | Cox et al. | |
| 2003/0101991 A1 | 6/2003 | Trueba | |
| 2005/0016550 A1 | 1/2005 | Katase | |
| 2005/0263618 A1 | 12/2005 | Spallek et al. | |
| 2006/0130860 A1 | 6/2006 | Cholet | |
| 2006/0196518 A1 | 9/2006 | Hon | |
| 2007/0062548 A1 | 3/2007 | Horstmann et al. | |
| 2007/0068523 A1 | 3/2007 | Fishman | |
| 2007/0074734 A1 | 4/2007 | Braunshteyn et al. | |
| 2007/0267031 A1 | 11/2007 | Hon | |
| 2008/0017193 A1 | 1/2008 | Jones et al. | |
| 2008/0092912 A1 | 4/2008 | Robinson et al. | |
| 2008/0168987 A1 | 7/2008 | Denny et al. | |
| 2008/0230052 A1 | 9/2008 | Montaser | |
| 2008/0241255 A1 | 10/2008 | Rose | |
| 2008/0257367 A1 | 10/2008 | Paterno et al. | |
| 2009/0126722 A1 | 5/2009 | Sugita et al. | |
| 2009/0272379 A1 | 11/2009 | Thorens et al. | |
| 2010/0108779 A1 | 5/2010 | Filsouf | |
| 2010/0200008 A1 | 8/2010 | Taieb | |
| 2010/0243754 A1 | 9/2010 | Harris | |
| 2010/0319686 A1 | 12/2010 | Schennum | |
| 2011/0011396 A1 | 1/2011 | Fang | |
| 2011/0036346 A1 | 2/2011 | Cohen et al. | |
| 2011/0094523 A1 | 4/2011 | Thorens et al. | |
| 2011/0155153 A1 | 6/2011 | Thorens et al. | |
| 2011/0226236 A1 | 9/2011 | Buchberger | |
| 2011/0232654 A1 | 9/2011 | Mass | |
| 2011/0265806 A1 | 11/2011 | Alarcon et al. | |
| 2012/0279990 A1 | 11/2012 | Werner et al. | |
| 2017/0351479 A1 | 12/2017 | Trejo | |
| 2019/0191779 A1 | 6/2019 | Alelov | |

FOREIGN PATENT DOCUMENTS

| | | |
|---|---|---|
| EP | 0358002 A2 | 3/1990 |
| EP | 0430566 A2 | 6/1991 |
| EP | 1211628 A2 | 6/2002 |
| EP | 1618803 A1 | 1/2006 |
| EP | 2022349 A1 | 2/2009 |
| EP | 2468116 A1 | 6/2012 |
| EP | 2982255 A1 | 2/2016 |
| EP | 3229623 A1 | 10/2017 |
| JP | 2005034021 A | 2/2005 |
| WO | 94/06314 A1 | 3/1994 |
| WO | 9418860 A1 | 9/1994 |
| WO | 9501137 A | 1/1995 |
| WO | 9920940 A1 | 4/1999 |
| WO | 0050111 A1 | 8/2000 |
| WO | 2007078273 A1 | 7/2007 |
| WO | 2009127401 A1 | 10/2009 |
| WO | 2010045671 A1 | 4/2010 |
| WO | 2010133342 A1 | 11/2010 |
| WO | 2011120085 A1 | 10/2011 |
| WO | 2012027350 A2 | 3/2012 |

OTHER PUBLICATIONS

Extended European Search Report of EP Application 11820510.3, dated Jan. 31, 2014.
Final Office Action on U.S. Appl. No. 13/460,982, dated Jan. 2, 2013.
Final Office Action on U.S. Appl. No. 13/460,982, dated Dec. 26, 2013.
International Search Report and Written Opinion issued in PCT/US2011/048782 dated Mar. 26, 2012.
Non-Final Office Action on U.S. Appl. No. 13/215,728, dated Oct. 15, 2012.
Non-Final Office Action on U.S. Appl. No. 13/460,982, dated Jun. 25, 2013.
Non-Final Office Action on U.S. Appl. No. 13/460,982, dated Sep. 4, 2012.
Notice of Allowance on U.S. Appl. No. 13/215,728, dated May 17, 2013.
Notice of Allowance on U.S. Appl. No. 13/460,982, dated Mar. 19, 2014.
Extended European Search Report for Application No. 19158504.1 dated Apr. 4, 2019, 6 pages.
Extended European Search Report for Application No. 19158505.8 dated Apr. 5, 2019, 6 pages.
Extended European Search Report for Application No. 19158510.8 dated Apr. 9, 2019, 6 pages.
Extended European Search Report for Application No. 19158512.4 dated Apr. 12, 2019, 6 pages.
Extended European Search Report for Application No. 19158517.3 dated Apr. 11, 2019, 8 pages.

(56) References Cited

OTHER PUBLICATIONS

Consolidated List of Cited Opposition Documents for Application No. EP15171948.1 dated Oct. 5, 2020, 2 pages.
Declaration by Julia E'Arcy dated Aug. 24, 2020, 1 page.
EP Register Extract of EP2982255B1.

\* cited by examiner

INHALATION DEVICE INCLUDING SUBSTANCE USAGE CONTROLS

CROSS-REFERENCE TO RELATED PATENT APPLICATIONS

This application is a continuation of U.S. patent application Ser. No. 14/257,079, filed Apr. 21, 2012, which is a continuation of U.S. patent application Ser. No. 13/460,982, filed May 1, 2012, now U.S. Pat. No. 8,714,150, which is a continuation of U.S. patent application Ser. No. 13/215,728, filed Aug. 23, 2011, now U.S. Pat. No. 8,550,069, which claims the benefit of the filing date of U.S. Provisional Application No. 61/402,136, filed Aug. 24, 2010, the disclosures of which are incorporated herein by reference in their entireties.

BACKGROUND

The present disclosure relates generally to the field of smoke inhalation devices and more particularly to control mechanisms for smoke inhalation devices.

Smoke inhalation devices, commonly known as e-cigarettes, can be used to simulate a cigarette or a cigar. For example, a smoke inhalation device can vaporize a liquid including nicotine. A user of the smoke inhalation device can inhale the vapor and have an experience similar to smoking a traditional cigarette or cigar.

SUMMARY

One illustrative embodiment is related to an apparatus including a first cartridge, a sensor, and a controller. The first cartridge can include a first release device configured to release a first substance into a housing. The controller can be configured to receive data from the sensor. The controller can determine an amount of first substance released by the first cartridge based on the data. The first release device can be controlled based on the determined amount of first substance.

Another illustrative embodiment is related to a method for metering an inhalation device. The method can include receiving data from a sensor. An amount of a first substance released by a first cartridge can be determined based on the data. The first cartridge can include a first release device configured to release the first substance into a housing. The first release device can be controlled based on the determined amount of first substance.

Another illustrative embodiment is related to a non-transitory computer-readable medium having instructions stored thereon that, if executed by a computing device, cause the computing device to perform operations for metering an inhalation device. The method can include receiving data from a sensor. An amount of a first substance released by a first cartridge can be determined based on the data. The first cartridge can include a first release device configured to release the first substance into a housing. The first release device can be controlled based on the determined amount of first substance.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION OF THE ILLUSTRATIVE EMBODIMENTS

Figure 1:
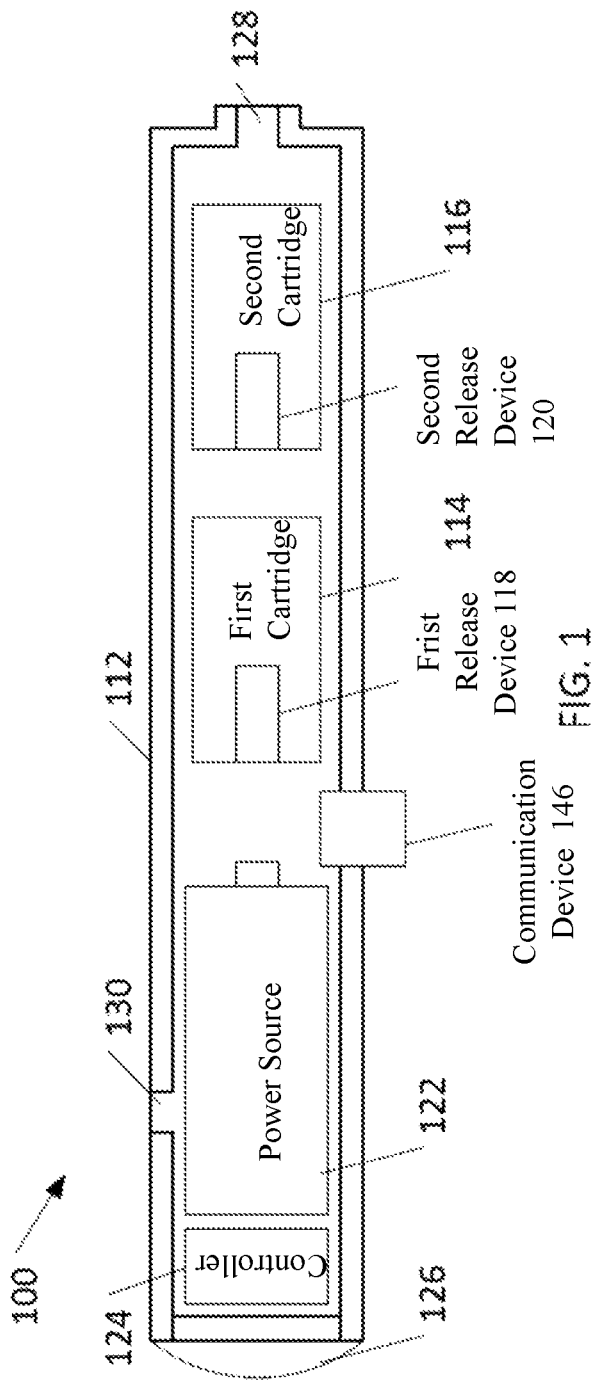
FIG. 1 is a section view of an inhalation device in accordance with an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

The present disclosure is directed to an inhalation device including a substance usage control mechanism. The inhalation device can comprise a housing to hold and contain parts, at least one cartridge containing a substance such as nicotine, at least one releasing device such as a heater or an atomizer to work with the cartridge, a power source such as a battery, and a controller. The controller can collect data and control the cartridge and the releasing device to deliver a predetermined amount of the substance to the user. The inhalation device can be a long cylindrical shape similar to a cigarette or cigar. Advantageously, the inhalation device can control and/or limit amount of substance delivered the usage to help the user limit the consumption of a certain substance such as nicotine. Advantageously, the inhalation device can control and/or limit amount of substance delivered such that a user can set a limit on an intake amount of the substance per use or for a certain period by the user. Advantageously, the inhalation device can receive and transmit data related to settings and usage. Advantageously, the inhalation device can monitor an amount of substance delivered to a user.

Referring to FIG. 1, a section view of an inhalation device 100 in accordance with an illustrative embodiment is shown. The inhalation device 100 can include a housing 112, a first cartridge 114, a second cartridge 116, a power source 122, a controller 124, a communication device 146, and a light device 126. In other embodiments, one or any number of cartridges can be used.

The housing 112 can be a long cylindrical shape, for example, the shape and size of a cigar, cigarillo, or cigarette. In other embodiments, the inhalation device 100 can be configured as other smoking or vapor delivery articles such as a hookah, a pipe, an inhaler, or a humidifier. The housing 112 can include an outlet hole 128 at a first end (i.e., a mouth end), where a user can place his lips to breathe in vapor or gas generated by inhalation device 100. The housing 112 can include an inlet hole 130 to allow air to enter the housing 112 when a user sucks on the first end. The housing 112 can be made of paper (e.g., paper rolled up in tubular shape), plastic, metal, wood, glass, or any other material.

The first cartridge 114 can be configured to retain and release a first substance such as nicotine. For example, the first cartridge 114 can include a medium such as a cotton fabric or a comparable material rolled up or shaped to fit inside housing 112. The cotton fabric can be soaked with the first substance. The first substance can include any drug, scent, transport agent, coloring, or a combination thereof. In one embodiment, the first substance is configured such that the substance can be vaporized or gasified. The first cartridge 114 can include a first release device 118. The first release device 118 can be embedded in or placed near the medium of the first cartridge 114. The first release device 118 can include one or a combination of a heating element, a vibration generator such as an ultrasonic or a piezoelectric transducer, an atomizer, or any other actuator to energize particles of the first substance such that the particles are released from the first cartridge 114 into a gas form or microscopic droplets that can be carried off by air stream, for example, an airstream between the inlet hole 130 and outlet hole 128. The first release device 118 can be configured to control or meter the amount or rate of first substance released from the first cartridge 114. In some embodiments, the inhalation device includes a single cartridge.

The second cartridge 116 can be configured to retain and release a second substance such as a scent. For example, the second cartridge 116 can include a medium such as a cotton fabric or a comparable material rolled up or shaped to fit inside housing 112. The cotton fabric can be soaked with the second substance. The second substance can include any drug, scent, transport agent, coloring, or a combination thereof. In one embodiment, the first substance and the second substance are difference substances. In another embodiment, the first substance and the second substance are the same substance. In one embodiment, the second substance is configured such that the substance can be vaporized or gasified. The second cartridge 116 can include a second release device 120. The second release device 120 can be embedded in or placed near the medium of the second cartridge 116. The second release device 120 can include one or a combination of a heating element, a vibration generator such as an ultrasonic or a piezoelectric transducer, an atomizer, or any other actuator to energize particles of the second substance such that the particles are released from the second cartridge 116 into a gas form or microscopic droplets that can be carried off by airstream, for example, an airstream between the inlet hole 130 and outlet hole 128. The second release device 120 can be configured to control or meter the amount or rate of second substance released from the second cartridge 116. The first cartridge 114 and the second cartridge 116 can be arranged such that the airstream passes over and/or through both the first cartridge 114 and the second cartridge 116. In other embodiments, the inhalation device can include multiple cartridges.

The power source 122 can provide power to the first cartridge 114, first release device 118, the second cartridge 116, second release device 120, the controller 124, the communication device 146, and the light device 126. The power source 122 can be a battery such as an alkaline battery, a nickel metal hydride battery, a lithium-ion battery, a rechargeable battery or any other energy source. In other embodiments, the power source 122 can be external to the housing 112.

The light device 126 is configured to simulate the burning on the tip of a cigar or cigarette. The light device 126 can include a light emitting diode (LED), a resistance-type lamp, an organic light emitting diode (OLED), or any other light emitting device. The light device 126 can be configured to vary intensity based on the amount of airflow between the inlet hole 130 and outlet hole 128.

The controller 124 can be configured to control the first release device 118, the second release device 120, the communication device 146, the power source 122, and the light device 126. The controller 124 can be operatively and communicatively coupled to the first release device 118, the second release device 120, the communication device 146, and the light device 126. The controller 124 can be a processor such as a central processing unit, an application specific integrated circuit (ASIC), a state machine or any other controller. The controller 124 can include memory which can be any type of permanent or removable computer memory known to those of skill in the art. The memory of controller 124 can be a computer-readable storage medium. The controller 124 can include software for controlling the first release device 118, the second release device 120, the communication device 146, and the light device 126, which can be implemented as computer-readable instructions configured to be stored on the memory of controller 124.

The communication device 146 can be configured to allow a user to change and monitor the settings and state of the inhalation device 100. For example, in one embodiment, communication device 146 can be used to reprogram a part of the control logic of controller 124 to limit the usage of the inhalation device 100. The communication device 146 can include at least one of a switch, a keypad, a display, an input/output port, and a wireless transceiver. In one embodiment, the input/output port and the wireless transceiver can be employed to create a communications link between the controller 124 and an external computer, such as a cell phone or personal computer.

Figure 2:
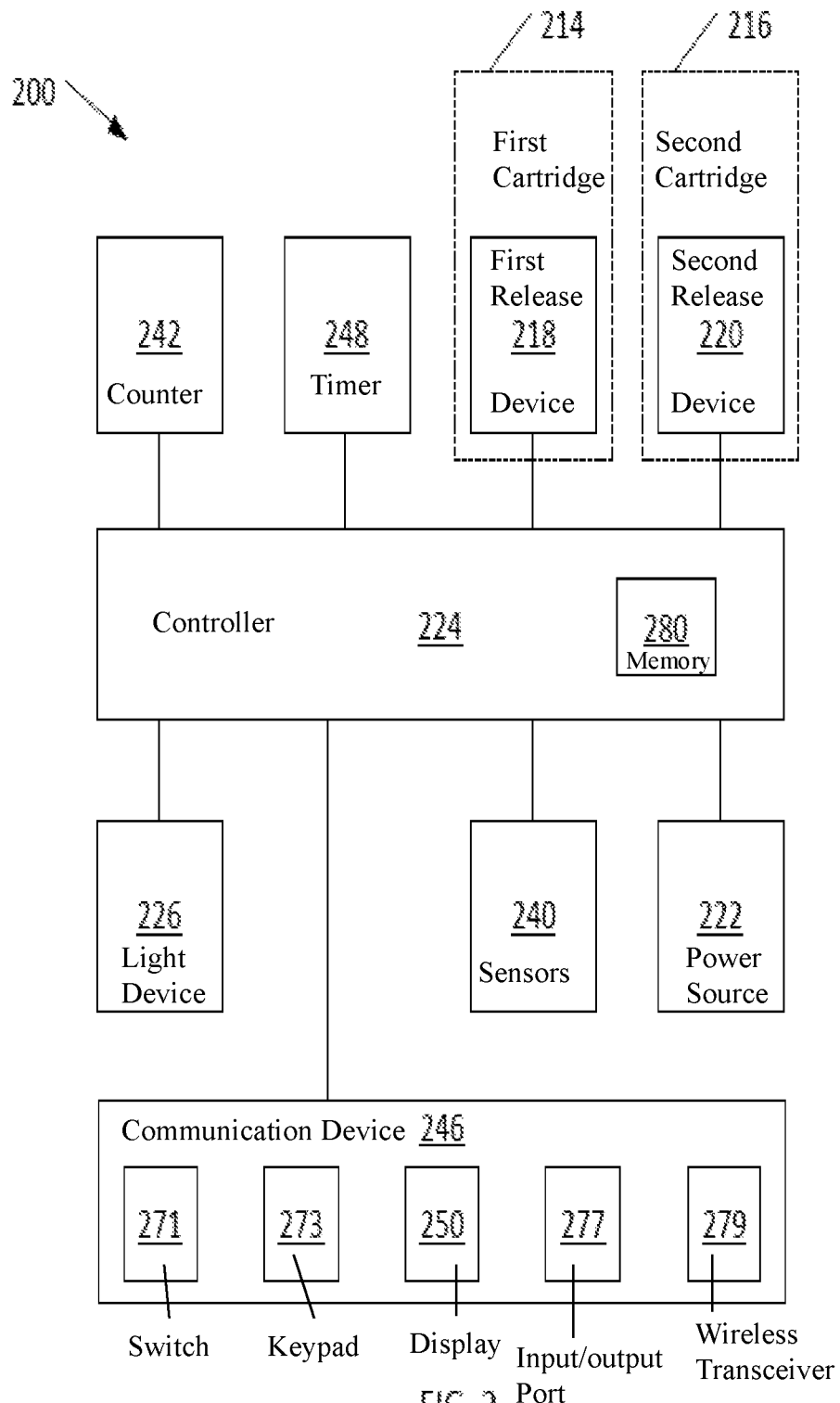
FIG. 2 is a schematic of an inhalation device control system in accordance with an illustrative embodiment.

Referring to FIG. 2, a schematic of an inhalation device control system 200 in accordance with an illustrative embodiment is shown. The inhalation device control system 200 can include a first release device 218 associated with a first cartridge 214, a second release device 220 associated with a second cartridge 216, a power source 222, a controller 224, a timer 248, a counter 242, sensors 240, a communication device 246, and a light device 226. The controller 224 can be operatively and communicatively coupled to the first release device 218, the second release device 220, the power source 222, sensors 240, the communication device 246, and the light device 226. The inhalation device control system 200 can be, for example, discrete, integrated as a chip, or a printed circuit board assembly.

The first cartridge 214 and second cartridge 216 may each contain a unique substance or a mixture of two or more substances and the mixture composition for one cartridge is different from another. For this reason, the first release device 218 and the second release device 220 can each be operated in a unique way to optimize the effect of the substance for the user. Furthermore, different techniques can be employed for releasing the substances of different cartridges.

Sensors 240 can be, for example, a flow sensor, a thermocouple or pressure sensor to detect the air stream passing through the device or a group of sensors to detect any one of or a combination of airflow, temperature change, pressure change, illumination of light, current change, voltage change, and other physical and electrical properties. Sensors 240 can be located within or on a housing associated with the inhalation device control system 200.

The controller 224 can be configured to control and monitor the first release device 218, the second release device 220, sensors 240, the communication device 246, the power source 222, and the light device 226. The controller 224 can be a processor such as a central processing unit, an application specific integrated circuit (ASIC), a state machine or any other controller. The controller 224 can include a memory 280 which can be any type of permanent or removable computer memory known to those of skill in the art. The memory 280 of controller 224 can be a computer-readable storage medium. The controller 224 can include software for controlling the first release device 218, the second release device 220, the communication device 246, and the light device 226, which can be implemented as computer-readable instructions configured to be stored on the memory 280 of controller 224.

The communication device 246 can include at least one of a switch 271, a keypad 273, a display 250, an input/output port 277, and a wireless transceiver 279. The input/output port 277 can be, for example, a serial port. The wireless transceiver 279 can be, for example, a Wi-Fi transceiver compliant with the IEEE 802.11 standard or a Bluetooth transceiver.

In one embodiment, the switch 271 can be a simple manual switch on a housing for sending reprogramming instructions to the controller 224 by clicking the switch 271 (e.g., clicking the switch five times with the clicking speed at one click per second or faster can reprogram the controller 224 to allow five puffs in a given period and then turn the device off). In another embodiment, the switch 271 can be a dial located on or in the middle of the housing for sending reprogramming instructions to the controller 224 such that by turning the dial the user can set the limit amount of the substance to be taken or inhaled. The dial switch can also be a section of the housing itself. In another embodiment, the switch 271 can be a shock or sound sensor such as a microphone for the user to tap for sending reprogramming instructions to the controller 224. The user can give the device taps at certain speed to set a desired amount of the substance to intake or inhale in a given period. In another embodiment, the switch 271 can be a light sensor to detect energy emitted by a laser, infrared, or other visible or invisible light source. Reprogramming instructions to the controller 224 can be on or off signals from the light source.

The user may use communication device 246 to reprogram the limit value in the controller 224. For example, a simple form of communication device 246 can be a manual switch the user can press or turn on or around the housing. By clicking or turning the switch manually, the user can change the limit setting in the controller 224. For example, by clicking the switch four times with a frequency of 1 Hz or higher, the user can smoke one cigarette equivalent worth of substance in each cycle or 10 each time, and clicking the switch two times will give a half cigarette worth of substance in each cycle. If the manual switch is a dial switch on the housing, the dial setting can set the limit. For example, the dial has indicator lines around it on the non-moving portion of the housing, and setting the dial at one can be equivalent to one cigarette dose per cycle and setting it to one half means a half of a cigarette dose.

The display 250 can be located on within or on the housing associated with the inhalation device control system 200. The display 250 can show messages indicating the usage to help the user keep track of his use of the device. The display 250 can be, for example, a light, a series of lights, a segmented display or a pixelated display. The display 250 can be made, for example, of LEDs, a LED panel, a liquid crystal display, a group of small light bulbs, or electronic ink. The display 250 can display indications to the user, for example, as letters, dots, symbols, a series of lines, figures, pictures, shapes or signals. The display 250 can be monotone or multi-colored.

The display 250 can indicate the usage level for the user to monitor the use of the device and can send out messages to encourage the user to cut down on the use based on the progress he or she makes. A display message can include a number of cigarette equivalents used or left on the inhalation device control system 200, a number of puffs (i.e., drags) used or left on the inhalation device control system 200, and it can include a real time display of a number of puffs the user is allowed to take in each cycle as he or she uses the inhalation device control system 200. This way the device alerts the user, as he or she uses it, how many cigarette equivalents he or she is taking in a given period since using the same device for a long time may lead the user to a false sense of the substance usage. For example, the inhalation device control system 200 with a full first cartridge 214 and second cartridge 216 can be equivalent to one pack of cigarettes and the display 250 can clearly indicate the number of cigarette equivalents or puffs left in the first cartridge 214 and second cartridge 216 as he or she uses the inhalation device control system 200.

The timer 248 can be configured to measure an amount of the substance disbursed and/or to meter a predetermined amount of the substance to a user. The timer 248 can be separate from or integrated with controller 224. The timer 248 can be configured to measure, for example, the amount of time elapsed between user puffs, the amount of time the first release device 218 and the second release device 220 are activated, and the time between uses.

The timer 248 can be configured to measure an amount of the substance disbursed and/or to meter a predetermined amount of the substance to a user. The timer 248 can be separate from or integrated with controller 224. The timer 248 can be configured to measure, for example, the amount of time elapsed between user puffs, the amount of time the first release device 218 and the second release device 220 are activated, and the time between uses. The timer 248 can be activated, for example, by an airflow sensor or a pressure switch. The timer 248 can be configured to measure a duration of a puff while the sensors 240 are activated.

The counter 242 can be configured to count a number of puffs taken per given period by a user. The counter 242 can be separate from or integrated with controller 224. The counter 242 can be configured to measure, for example, a number of puffs taken by a user during a smoking session, a day, a week, a month, or any other time period. The counter 242 can be activated, for example, by sensors 240.

For a more precise control of the amount of the substance allowed in a given period, timer 248 can be used to time the airflow through the device. Each time sensors 240 such as a flow sensor or a pressure switch are activated by the airflow, timer 248 can measure the duration of the airflow and the time for duration can be accumulated in a given period to activate a limit feature according to a substance distribution limit set in the control logic. Also counter 242 can be used to count the number of activations of sensors 240.

Counter 242 and timer 248 can provide usage data on the number of puffs per given period and timer 248 can provide both time duration of airflow for each puff and total time accumulated for the airflow over a given period. Therefore, when the substance distribution limit is set by the user or preset by the factory, the limit can be set on the actual amount of the substance in terms of total time allowed for airflow within a given period for use, not just an allowable number of puffs. Since an amount of airflow for a puff is different from person to person, setting a number of puffs as a limit can allow different amount of the targeted substance delivered to each different user or even to a same user depending on duration of each and every puff. Therefore, using timer 248 to monitor the usage along with counter 242 can provide a more accurate estimate of the measurement of the total airflow.

The inhalation device control system 200 can come with a factory setting for the allowable amount of the substance contained in the cartridges (214, 216) to be released. Different users have different usage habits: One person may prefer long hard puffs and another person may like short shallow puffs. A person having long hard puffs usually finishes a cigarette in a less number of puffs than the person having the short shallow puffs. For this reason, the amount of substance allowed can be set as total duration time that is a time accumulation value of the total puffs in a given period. Another sensor such as a current sensor for the releasing means or the power source or a flow sensor with the air speed measurement can be applied to estimate the quantity of the substance use whenever the user draws the air through the device, and this information can be used along with the timer to calculate the more accurate amount of the substance use. Once the limit value as the time accumulation is set, timer 248 measures the duration of each puff and send the data to the control logic in controller 224 and controller 224 accumulates and compares the accumulated data with the set limit value. Once the accumulated time value or the value calculated from a combination with the accumulated time and the data of the quantity of the substance from the sensor reaches or goes over the limit value, controller 224 turns the inhalation device control system 200 off or makes the inhalation device control system 200 go into a low level mode in which the inhalation device control system 200 releases the substance at a lower rate than during the earlier period. The limit value can be set with cycles. For example, once the device is on, the user can be allowed a first set time limit for the total duration time of puffs within five minutes that is roughly equal to smoking one cigarette, and within a given period such as twelve hours or a day, the user can be allowed to use the inhalation device control system 200 a set number of times. Once the limit is reached controller 224 can turn off the releasing means (218, 220) to stop the substance flow to the user until the next cycle begins after non smoking time expires between two consecutive cycles or controls the releasing means (218, 220) such that the substance flow to the user is more limited per puff until the next cycle begins.

Figure 3:
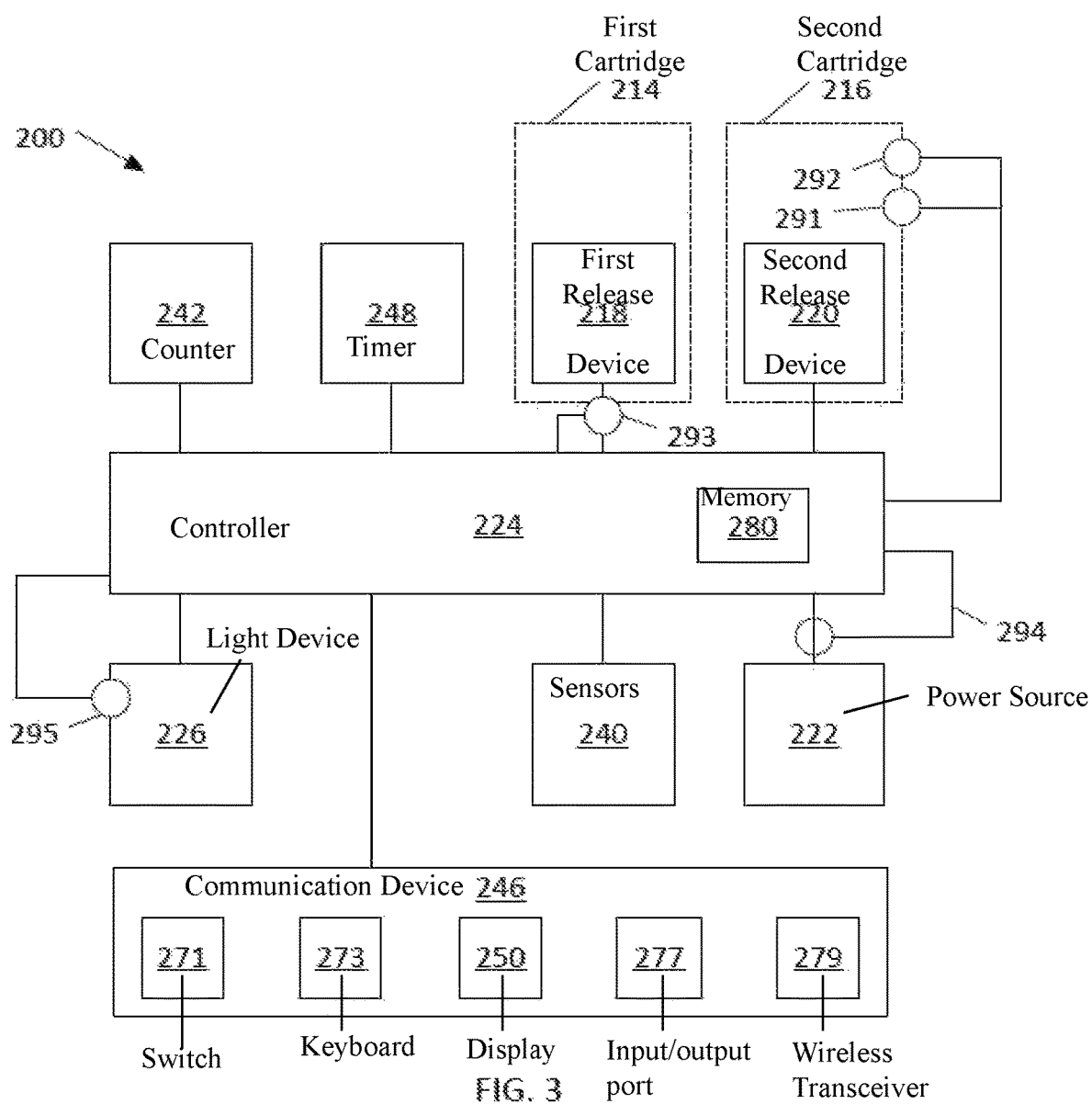
FIG. 3 is a schematic of the inhalation device control system of FIG. 2 with additional sensors in accordance with an illustrative embodiment.

Referring to FIG. 3, a schematic of the inhalation device control system 200 of FIG. 2 with additional sensors in accordance with an illustrative embodiment is shown. The inhalation device control system 200 can include a first release device 218 associated with a first cartridge 214, a second release device 220 associated with a second cartridge 216, a power source 222, a controller 224, a timer 248, a counter 242, sensors 240, a communication device 246, and a light device 226. The controller 224 can be operatively and communicatively coupled to the first release device 218, the second release device 220, the power source 222, sensors 240, the communication device 246, and the light device 226. The communication device 246 can include at least one of a switch 271, a keypad 273, a display 250, an input/output port 277, and a wireless transceiver 279. As discussed further below, the inhalation device control system 200 can measure substance usage in ways other than using a flow sensor or a pressure switch.

The first release device 218 and the second release device 220 can release a first substance from the first cartridge 214 and a second substance from the second cartridge 216 using, for example, heat and/or vibration. A temperature sensor 291 located on the second cartridge 216 can be used to detect the temperature of the second cartridge 216. The controller 224 can estimate an amount of substance released by the second cartridge 216 based on temperature information from the temperature sensor 291, along with information from timer 248. A vibration sensor 292 located on the second cartridge 216 can be used to detect the agitation of the second cartridge 216. The controller 224 can estimate an amount of substance released by the second cartridge 216 based on agitation information from the vibration sensor 292, along with information from timer 248. A current sensor 293 located on the power feed to the first release device 218 can be used to determine the current used by the first release device 218. The controller 224 can estimate an amount of substance released by the first cartridge 214 based on current information from the current sensor 293. Alternatively, a voltage sensor can be used.

In another embodiment, a current sensor 294 located on the power feed from power source 222 can be used to estimate the current used by the first release device 218 and second release device 220. The controller 224 can estimate an amount of substance released by the first cartridge 214 and the second cartridge 216 based on current information from the current sensor 294. Alternatively, a voltage sensor can be used. In another embodiment, a light sensor 295 located in proximity to light device 226 can be used to estimate the usage of the first release device 218 and second release device 220. The controller 224 can estimate an amount of substance released by the first cartridge 214 and the second cartridge 216 based on the amount of time the light sensor 295 is activated as well as the intensity detected by the light sensor 295. Alternatively, other sensors can be used as is known in the art. Alternatively, sensors 291-295 can be place in various locations as is known in the art.

An illustrative inhalation device package for the market can be, for example, a smoking device in a cigarette form that comes with a capacity for smoking about twenty cigarettes. A factory setting can be preloaded to the smoking device to allow about fifteen puffs per use within five minutes, and after the user is done smoking for the time, he or she has to wait at least 30 minutes before using the device again. A display on the inhalation device can show the number of cigarette equivalents left to go, and it can also show the user the number of puffs left to go before the current use is expired as he or she use the inhalation device. In such a setting, the inhalation device can be programmed to monitor the usage of the substance contained in a cartridge by measuring the number of intake, or calculating the quantity of consumption of the substance from data collected from timer for the duration of each and every intake of the air and another sensor such as a electric current sensor or air flow sensor for the rate of flow of the substance. The number of puffs can then be translated to actual substance used based on the calculated estimation from the data provided by the timer and the sensor. Also a counter in the system can be used to count the number of intakes to provide the data to the control means to make calculation simpler. The user may use a button or a dial to change the factory settings such as the number of puffs allowed per use (e.g., from fifteen puffs setting to twenty puffs) and the duration of off time after the use before the next use is permitted (e.g., 30 minutes factory setting to 45 minutes or to 15 minutes). There can be one or more buttons or dials on the inhalation device to reprogram the settings for the inhalation device. A first button or dial for setting the off time duration and a second button or dial for setting a number of puffs allowed per use or other settings depending on the user preference and convenience.

Figure 4:
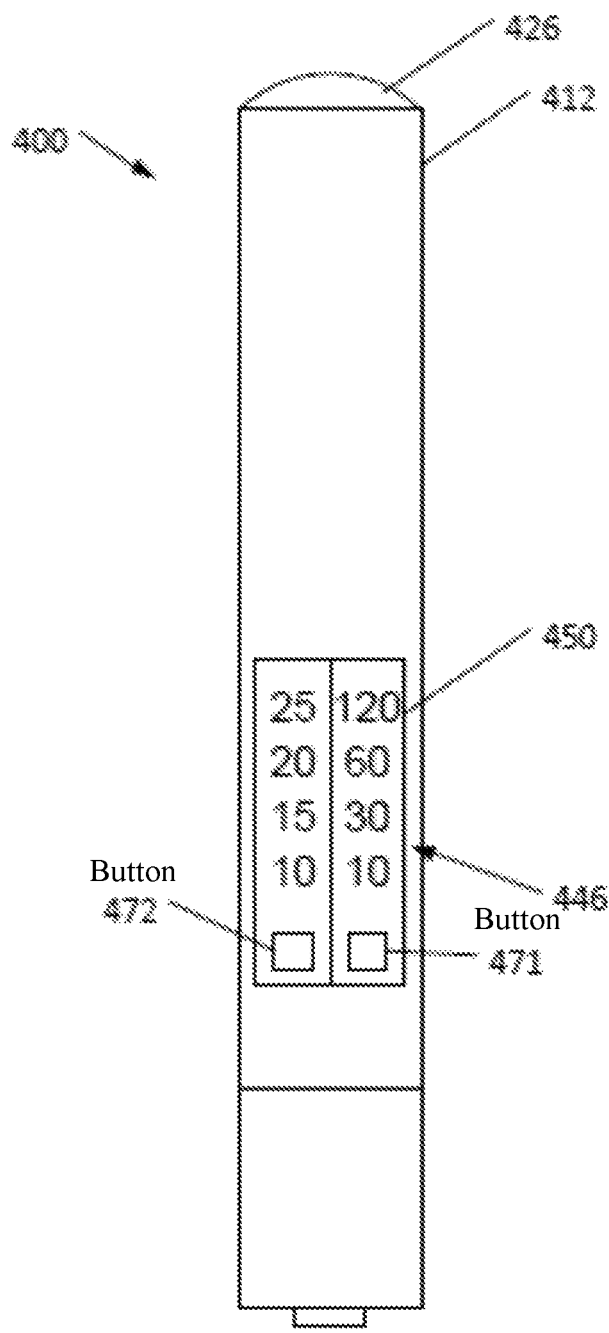
FIG. 4 is a diagram of a first inhalation device in accordance with an illustrative embodiment.

FIGS. 4 through 8 depict a number of different illustrative embodiments of the inhalation device. Referring to FIG. 4, a diagram of a first inhalation device 400 in accordance with an illustrative embodiment is shown. The first inhalation device 400 can include a housing 412, a communication device 446, and a light device 426. The communication device 446 can include a display 450 and buttons 471 and 472. The first inhalation device 400 has two separate programming modes. In a first mode, button 471 can be used to change the limit for a number of puffs allowed per use. In a second mode, button 472 can be used to change the amount of shut off time required before the next use. The display 450 can display an indication of a setting. (e.g., "10," "30," "60," "120," "10," "15," "20," "25")

Figure 5:
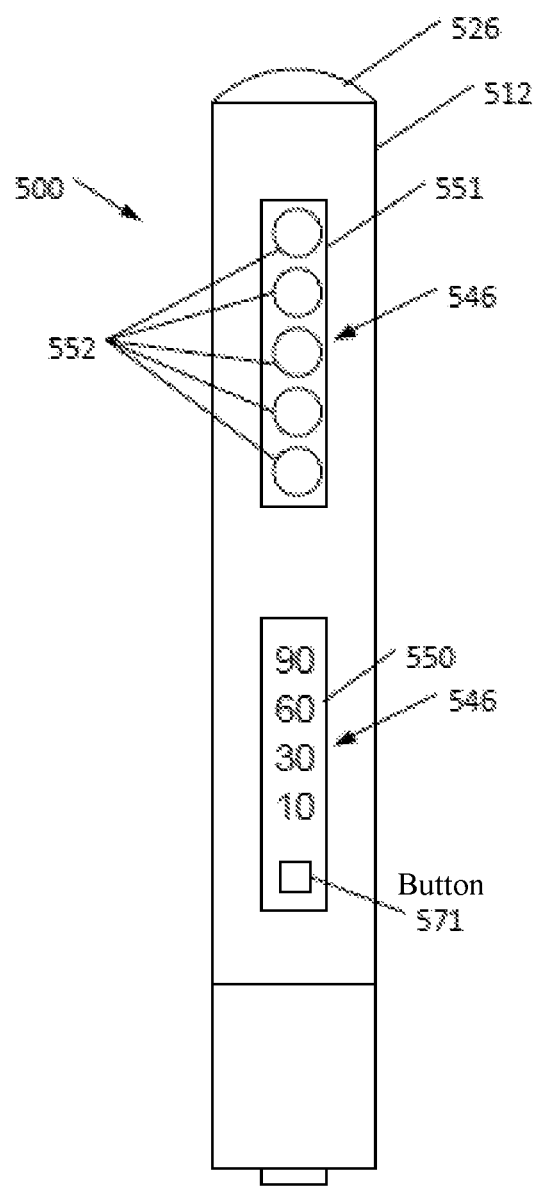
FIG. 5 is a diagram of a second inhalation device in accordance with an illustrative embodiment.

Referring to FIG. 5, a diagram of a second inhalation device 500 in accordance with an illustrative embodiment is shown. The second inhalation device 500 can include a housing 512, a communication device 546, and a light device 526. The communication device 546 can include a first display 550, a button 571, and a second display 551. The button 571 can be used to change the amount of shut off time required before the next use. The first display 550 can display an indication of a setting. (e.g., "10," "30," "60," "90") The second display 551 can include lights 552. The lights 552 can indicate the indicating the number of cigarette equivalent remaining in the second inhalation device 500.

Figure 6:
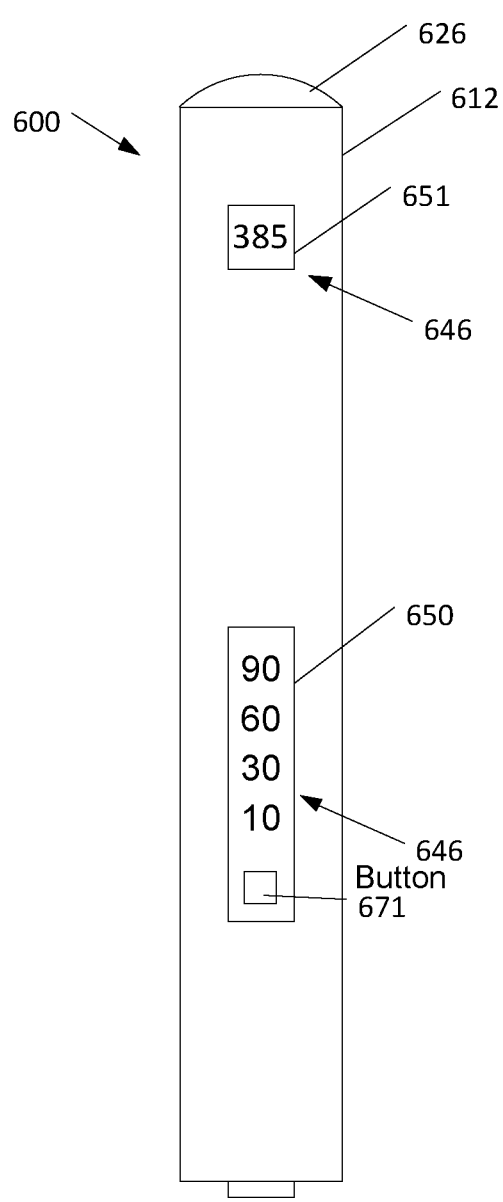
FIG. 6 is a diagram of a third inhalation device in accordance with an illustrative embodiment.

Referring to FIG. 6, a diagram of a third inhalation device 600 in accordance with an illustrative embodiment is shown. The third inhalation device 600 can include a housing 612, a communication device 646, and a light device 626. The communication device 646 can include a first display 650, a button 671, and a second display 651. The button 671 can be used to change the amount of shut off time required before the next use. The first display 650 can display an indication of a setting. (e.g., "10," "30," "60," "90") The second display 651 can display an indication (e.g., "385") showing the number of puffs or substance quantity remaining or available in the second inhalation device 600.

Figure 7:
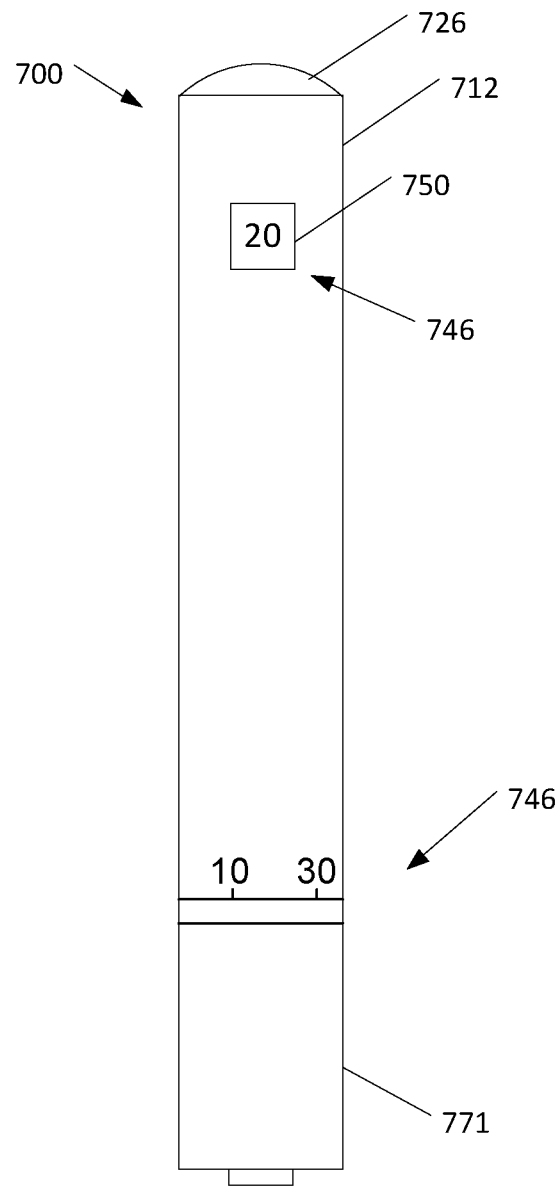
FIG. 7 is a diagram of a fourth inhalation device in accordance with an illustrative embodiment.

Referring to FIG. 7, a diagram of a fourth inhalation device 700 in accordance with an illustrative embodiment is shown. The fourth inhalation device 700 can include a housing 712, a communication device 746, and a light device 726. The communication device 746 can include a first display 750 and a dial 771. The dial 771 can be implemented as part of the housing 712. For example, a bezel of the dial 771 can be located at a filter area of the housing 712. The housing 712 can include graduation markings (e.g., "10," "30") near the dial 771. The dial 771 can be used to change the amount of shut off time required before the next use. The first display 750 can display an indication (e.g., "20") showing the number of cigarette equivalents remaining or available in the fourth inhalation device 700.

Figure 8:
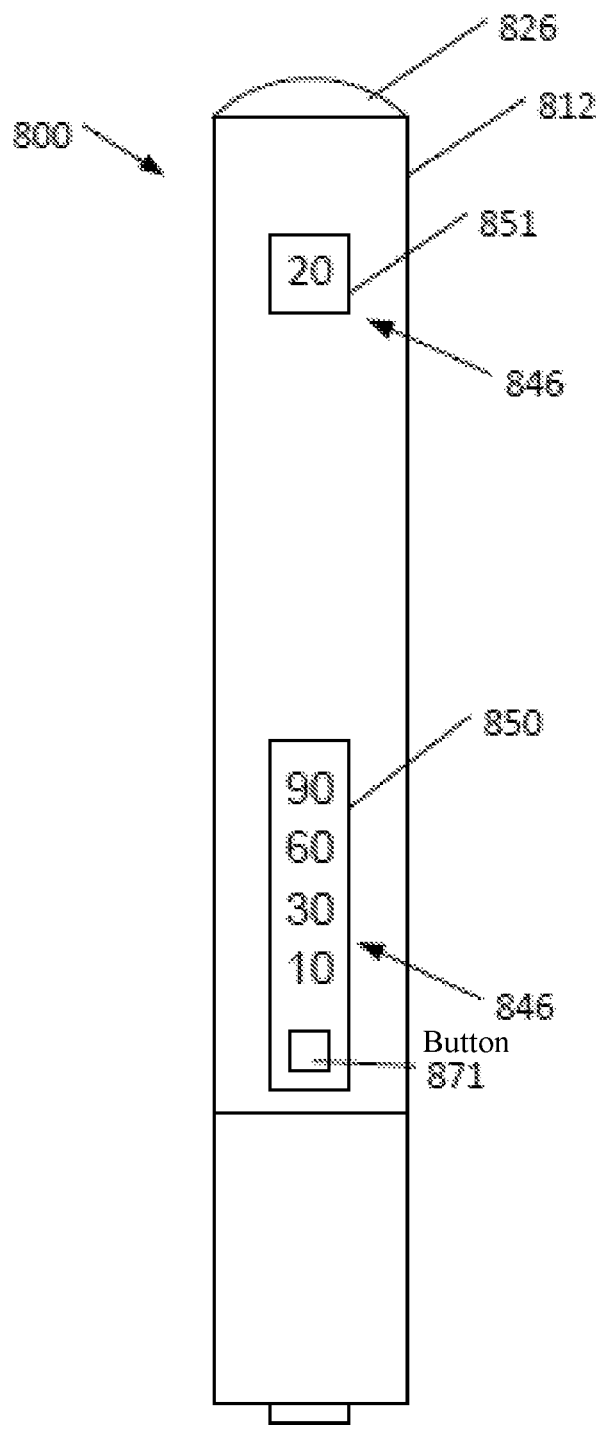
FIG. 8 is a diagram of a fifth inhalation device in accordance with an illustrative embodiment.

Referring to FIG. 8, a diagram of a fifth inhalation device 800 in accordance with an illustrative embodiment is shown. The fifth inhalation device 800 can include a housing 812, a communication device 846, and a light device 826. The communication device 846 can include a first display 850, a button 871, and a second display 851. The button 871 can be used to change the usage limit settings by the user. The first display 850 can display an indication of a setting. (e.g., "10," "30," "60," "90") The second display 851 can display an indication (e.g., "20") showing the number of cigarette equivalents remaining or available in the fifth inhalation device 800.

Figure 9:
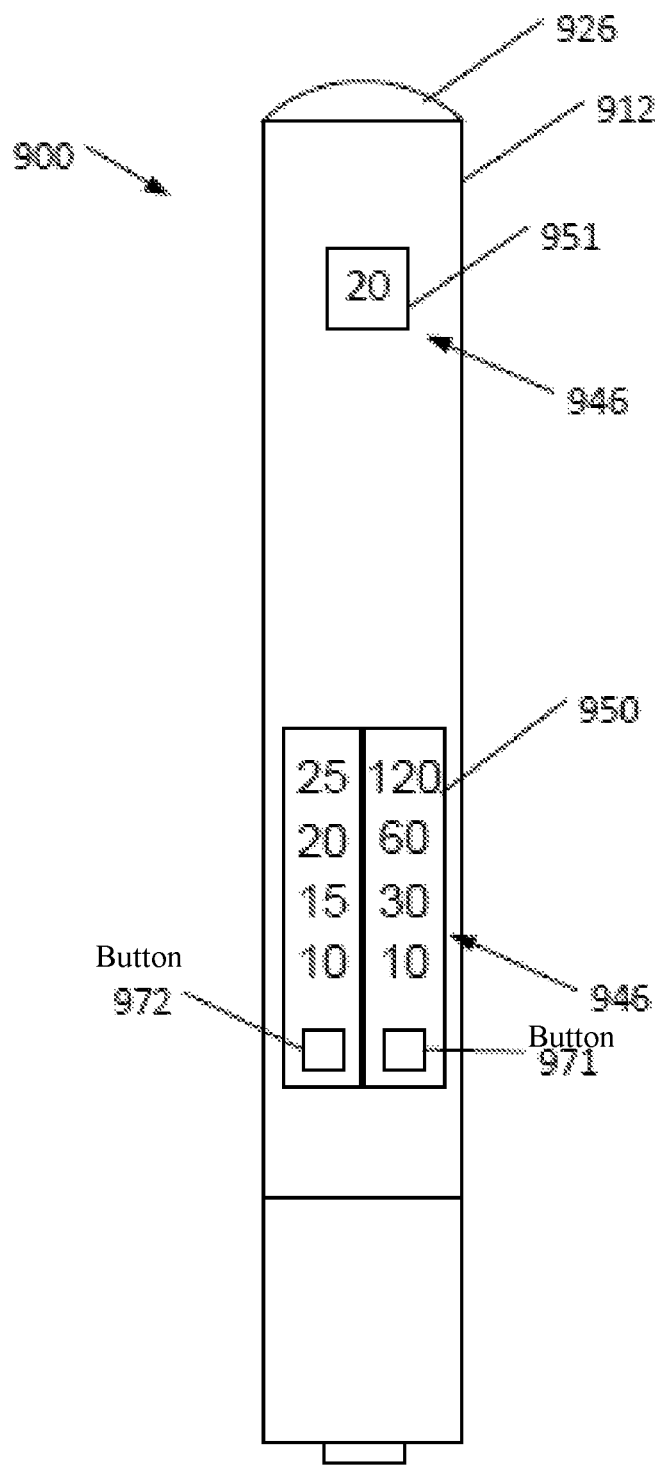
FIG. 9 is a diagram of a sixth inhalation device in accordance with an illustrative embodiment.

Referring to FIG. 9, a diagram of a sixth inhalation device 900 in accordance with an illustrative embodiment is shown. The sixth inhalation device 900 can include a housing 912, a communication device 946, and a light device 926. The communication device 946 can include a first display 950, buttons 971 and 972, and a second display 951. The sixth inhalation device 900 has two separate programming modes. In a first mode, button 971 can be used to change the limit for a number of puffs allowed per use. In a second mode, button 972 can be used to change the amount of shut off time required before the next use. The first display 950 can display an indication of a setting. (e.g., "10," "30," "60," "120," "10," "15," "20," "25") The second display 951 can display an indication (e.g., "20") showing the number of cigarette equivalents remaining or available in the sixth inhalation device 900.

One or more flow diagrams may have been used herein. The use of flow diagrams is not meant to be limiting with respect to the order of operations performed. The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A smoke inhalation apparatus comprising:
 a cartridge comprising a release device configured to release a substance;
 a controller configured to control the operation of the release device; and
 a communication device configured to allow a user to change and monitor settings of the smoke inhalation apparatus and/or a state of the smoke inhalation apparatus, the communication device including a display configured to indicate usage of the smoke inhalation apparatus, the communication device being configured to reprogram the controller to operate according to a modified usage limit different than an initial usage limit.

2. The smoke inhalation apparatus according to claim 1, wherein the communication device further comprises a manual switch operable to set an amount of the substance to be inhaled.

3. The smoke inhalation apparatus according to claim 2, wherein the switch is a dial configured to reprogram the controller based on turning of the dial by a user.

4. The smoke inhalation apparatus according to claim 3, wherein the dial is a section of a housing of the smoke inhalation apparatus, the cartridge being contained within the housing.

5. The smoke inhalation apparatus according to claim 1, wherein the communication device further comprises a light sensor operable to set an amount of the substance to be inhaled.

6. The smoke inhalation apparatus according to claim 1, wherein the communication device further comprises two manual switches, a first of the switches being operable to set a time duration of a smoking cycle, and a second of the switches being operable to set a number of puffs a user is permitted to take during the smoking cycle.

7. The smoke inhalation apparatus according to claim 1, wherein the display is configured to indicate a consumed amount of the substance.

8. The smoke inhalation apparatus according to claim 7, wherein the consumed amount is displayed in cigarette equivalents or number of puffs.

9. The smoke inhalation apparatus according to claim 7, wherein the display is located within a housing of the smoke inhalation apparatus, the cartridge being contained within the housing.

10. The smoke inhalation apparatus according to claim 7, wherein the display is configured to indicate a number of puffs a user is permitted to take during a smoking cycle.

11. A method of changing settings for a smoke inhalation apparatus having a cartridge comprising a release device configured to release a substance into a housing, the method comprising:
 displaying information on a communication device of the smoke inhalation apparatus, the information indicating usage of the smoke inhalation apparatus;
 receiving input from a user through the communication device; and
 reprogramming the controller to operate according to a modified usage limit different than an initial usage limit, based on the input from the user.

12. The method according to claim 11, further comprising receiving input from a user that sets an amount of the substance to be inhaled.

13. The method according to claim 11, wherein the reprogramming of the controller is actuated by turning of a manual dial by the user.

14. The method according to claim 13, wherein the dial is a section of a housing of the smoke inhalation apparatus, the cartridge being contained within the housing.

15. The method according to claim 11, wherein the reprogramming of the controller is actuated by a light sensor.

16. The method according to claim 11, further comprising setting a time duration of a smoking cycle and/or setting a number of puffs a user is permitted to take during the smoking cycle.

17. The method according to claim 11, wherein the displaying information includes indicating a consumed amount of the substance.

18. The method according to claim 17, wherein the consumed amount is displayed in cigarette equivalents or number of puffs.

19. The method according to claim 17, wherein the display is located within a housing of the smoke inhalation apparatus, the cartridge being contained within the housing.

20. The method according to claim 17, wherein the displaying information includes displaying a number of puffs a user is permitted to take during a smoking cycle.

* * * * *